United States Patent [19]
Strauss et al.

[11] Patent Number: 6,046,050
[45] Date of Patent: Apr. 4, 2000

[54] HUMAN LIVER CELL LINE

[75] Inventors: Michael Strauss, Berlin, Germany; Ira Kirillowa, Seattle, Wash.

[73] Assignee: HepaVec AG für Gentherapie, Germany

[21] Appl. No.: 09/035,396

[22] Filed: Mar. 5, 1998

[30] Foreign Application Priority Data

Mar. 5, 1997 [DE] Germany .............. 197 11 266

[51] Int. Cl.$^7$ .............. C12N 15/85; C12N 15/00; C12Q 1/68; C07H 21/04
[52] U.S. Cl. .............. 435/467; 435/6; 435/325; 435/370; 435/375; 435/455; 536/24.5
[58] Field of Search .............. 435/6, 69.1, 440, 435/455, 325, 366, 467, 370, 375, 320.1; 536/23.1, 23.5, 24.5

[56] References Cited

FOREIGN PATENT DOCUMENTS

WO 94/20607   9/1994   WIPO .

OTHER PUBLICATIONS

Woodworth et al. Molecular and Cellular Biology, Oct. 1988, vol. 8, No. 10, pp. 4492–4501.

Wu et al. Cancer Research, Nov. 1994, vol. 54, pp. 5964–5973.

*Primary Examiner*—John L. LeGuyader
*Assistant Examiner*—Mark L. Shibuya
*Attorney, Agent, or Firm*—Londa and Traub LLP

[57] ABSTRACT

The invention refers to a new human liver cell line which may be used for toxicological, physiological and, in particular, gene therapeutic examinations. Fields of application are molecular biology, medicine and pharmaceutical industry. The new human liver cell line is marked positive owing to the parameters albumin and alpha-1-antitrypsin (ATT) and negative owing to alpha-fetoprotein (AFP). It has been deposited in the Deutsche Sammlung von Mikroorganismen (DSM ACC2302).

3 Claims, 5 Drawing Sheets

(2 of 5 Drawing Sheet(s) Filed in Color)

HUMAN LIVER CELL LINE

BACKGROUND OF THE INVENTION

The invention refers to a new human cell line which may be used for toxicological, physiological and especially gene therapeutic examinations. Fields of application are molecular biology, medicine and pharmaceutical industry.

Gene therapy of liver diseases is an important target of molecular medicine as a multitude of genetic diseases, yet also infectious and tumor diseases, start from this organ. In the last few years, on international scale, the, first of all, expensive way of the ex vivo gene therapy was opened up, with a part of the liver being removed and the cells isolated from it being treated by the therapeutic gene in the cell culture and subsequently transplanted back into the liver. It is comparatively easy to transfer genes in cells in culture by various physical or chemical aids. Yet, the highest efficiency is reached by means of vectors coming from viruses which were modified in a purposeful way by means of gene technology. Thereby, retroviruses and adenoviruses were especially successfully used. As, on international scale, the way of ex vivo gene therapy has not proved to be sufficiently effective to allow a therapeutic effect of the gene transfer the in vivo gene transfer is the only solution. In addition to using adenoviruses which show a comparatively high affinity to liver a number of other viruses were tested as to their being suited as transfer vehicles.

Dividing differentiated hepatocytes are required for such testing. For a long time there has been tried to establish lines of differentiated hepatocytes of rodents and men.

During the last ten years there was stated that the transformation of various cell types by SV40 is a way of establishing cells which frequently results in the loss of the cell type-specific functions.

In 1986 primary hepatocytes of a rat were established as a line by means of transfection of SV40 DNA. the hepatocytes maintained their ability to produce albumin, transferrin and glucose-6-phosphatase and not to express AFP (carcinoembryonic protein). Yet, these cells showed features of transformed cells —they grew in soft agar and formed tumours in hairless mice (Woodworth et al., 1986).

In 1988 there was attempted to express the SV40 T-Ag from the embryonic liver of transgenic mice. This was an alternative method to immortalize primary hepatocytes after having been put in culture. It was assumed that the hepatocytes of transgenic mice were already immortalized in vivo. This is a possibility to avoid the loss of differentiated parameters in cultivated primary hepatocytes. The cells of the established hepatocyte lines produced albumin. They have not grown in soft agar and did not form tumours in hairless mice. This fact points to the fact that the immortalizing and transforming function of the T-Ag may be separated from each other. However, after subcloning the cells show the properties of transformed cells (Paul et al., 1988). In addition, the cells of this line coming from embryonic liver and being positive for AFP may not be regarded as differentiated hepatocytes.

In 1993 it was possible to immortalize human hepatocytes by SV40 T-Ag by means of retroviral infection. The THLE-2 and -3 lines obtained were not tumoural in hairless mice and did not express AFP. The cells of earlier passages (inoculations) were in a position to produce albumin and cytokeratin 8 (CKN8, characteristic of hepatocytes) and to metabolize a number of chemical cancerogenes. In cells of later passages the expression of cytokeratin (CKN19, characteristic of bile-duct epithelium) and a reduction of the albumin expression were observed (Pfeifer et al., 1993).

Two lines of differentiated, immortalized hepatocytes were obtained from transgenic mice who expressed the gene for the hepatocyte growth factor TGF-α. The cells of the two AML-12 and AML-14 lines were not tumoural in hairless mice and expressed mRNA for albumin, α-1 -antitrypsin (AAT) and transferrin. However, with the number of passages increasing the expression of the hepatocyte-specific genes declined (Wu et al., 1994).

To sum up there can be stated that the known liver cell lines may not be satisfactory in many respects.

SUMMARY OF THE INVENTION

The invention is aimed at establishing a new human liver cell line which may be used for toxicological, physiological and, in particular, gene therapeutic examinations.

The invention is based on the task to reach this aim by affecting genetically the cell cycle regulation of human hepatocytes.

This task was accomplished by developing the human liver cell line HepZ according to the invention. This new cell line was deposited in the Deutschen Sammlung von Mikroorganismen and Zellkulturen (DSMZ =German collection of microorganisms and cell cultures) located at Mascheroder Weg 1b, D-38124 Braunschweig, on March 4, 1997,by the registration number DSM ACC2302.

Detailed Description of the Invention

To obtain the cell line proceeding from primary human hepatocytes the following steps were undertaken according to the invention (which are also generally applicable to liver cells):

stimulation of a cell division round by hepatocyte growth factor (HGF), subsequent or simultaneous transfection of the antisense coding recombinants AlbasRb and Albasp53 and optionally additional transfection with recombinants bringing about the expression of cyclin D1 and/or E2F.

In particular, they are obtained as follows: In preliminary experiments primary human hepatocytes were cotransfected by the following plasmides:

pAlbasRb
pSV2neoD1
pCMVE2F

Figure 1:
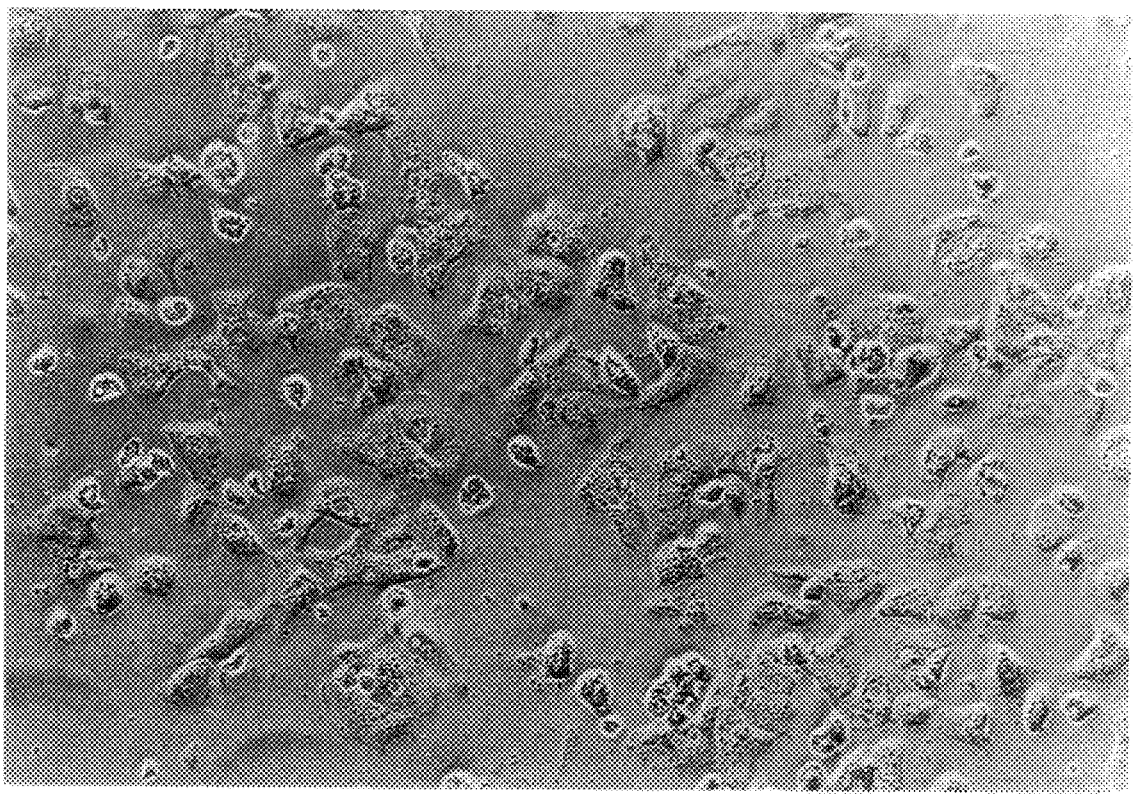
FIG.1 Prolongation of the life span of primary human hepatocytes up to 6 weeks by means of transfection of the plasmide combination: pAlbas Rb +pSV2neoD1 +pCMVe2F. (enlargement 1:100)

A prolongation of the life span of the cells up to 6 weeks was achieved while maintaining their morphology, yet an intensified permanent proliferation was not reached (FIG. 1). Thereupon a degeneration of the cells was observed.

With the aim to avoid the apoptotic death of the genetically modified primary hepatocytes the expression of gene p53 was additionally blocked.

This blocking was reached in the following way: The hepatocytes extracted from the liver segment were sown with a cell density of $5 \times 10^5$ per 6 cm of pan and for 2 hours cultivated with WM E with growth factors and 10 % of FKS. Two hours after plating the medium was replaced by serum-free WM E. HGF (10 ng/ml) was added to the medium. It is known that the HGF level in the serum will rise during the first hours after the partial resection of the liver. Only 24 –48 hours (in various species) after the operation the peak of the DNA synthesis will be reached; i.e. approx. 20–40 hours after the HGF effect set in. It was expected that the peak of the DNA synthesis in primary human hepatocytes caused by plating and the effect of HGF should be detected also in the same period.

On the day following the plating and addition of HGF the transfection of the hepatocytes was effected by means of lipofectamine with the following plasmids (at a ratio 1:1:1:1):

AlbasRb
Albasp53
pCMVE2F
pSV2neoD1

As the frequency of immortalizing primary human cells is very low hepatocytes were transfected in 5 pans (total cell quantity $2.5 \times 10^6$). In addition, also 10% of FKS were added to the medium (and also growth factors) 5 hours after the transfection when replacing the medium. 18 days after the transfection the biggest part of the transfected cells was degenerated (whereas the hepatocytes in the control pans maintained their viability up to 6 weeks). During this time, a formation of 4 colonies was observed only in one pan. One of the colonies was transferred to a 24 "well" plate. Fresh WM E and conditioned supernatant liquid of the colonies formed were added to these cells (at a ratio 1: 1). The cells grew on and after 2 days the number of cells had doubled. In the center of the colony the morphology of the cells was very similar to that of primary hepatocytes whereas the cells situated at the periphery of the colony were largely stretched out. In the second week the cells of the colony had rounded and scaled off the pan surface whereupon the cell death was observed.

Figure 2:
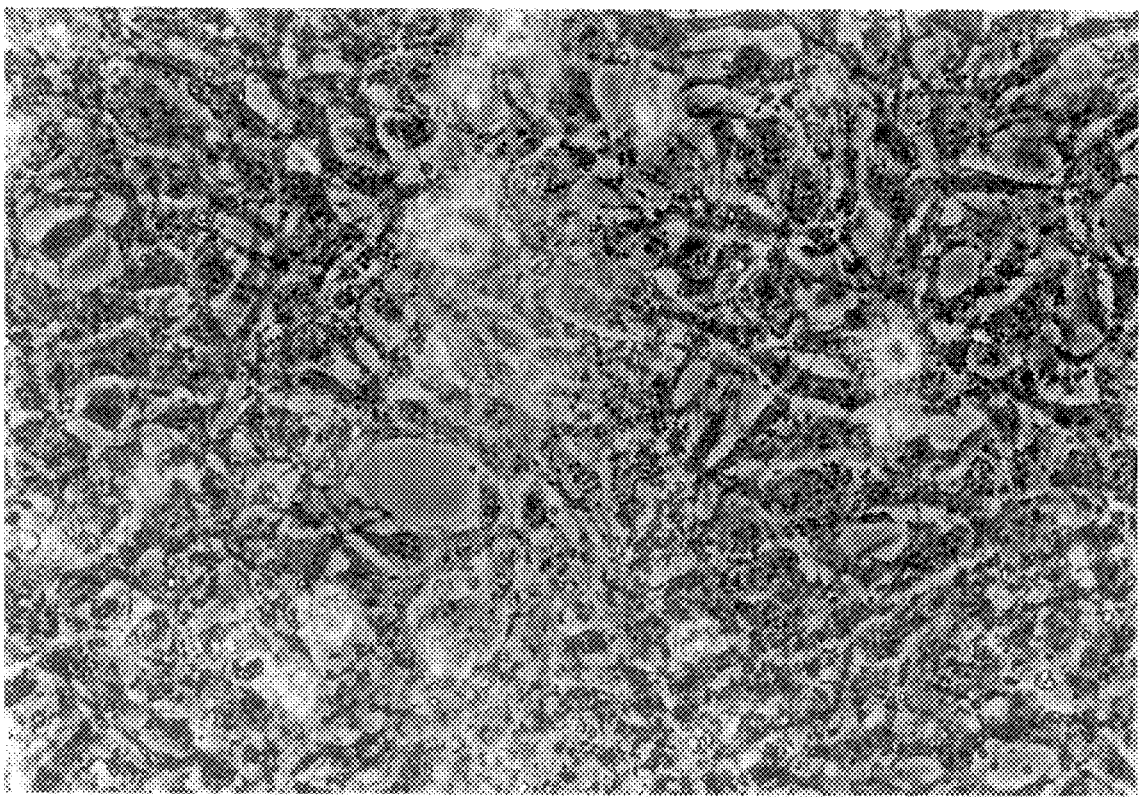
FIG. 2 HepZ hepatocyte line established from primary human hepatocytes by means of transfection brought about by lipofectamine with the plasmide combination: pAlpasp53 +pAlbas Rb +pCMVE2F +pSV2neoD1 (after 15 passages) (enlargement 1:100)

At the same time, a proliferation of the cells of the last colony was observed in the initial pan. Sufficient asp53 was expressed presumably only at an extremely low percentage of the cells to save cells from apoptosis. After 10 days the cells reaching subconfluence were inoculated. After the passage (inoculation) the cells did no longer form compact colonies. The cell doubling time was short and passages were going on 2 times a week. Up to 3 passages the cells depended on growth factors and serum and did not grow in the event of the cell density being low ($3 \times 10^4$ cells per 6 cm of pan). After 7 passages the growth of the cells was independent of insulin. The morphology of the cells is similar to that of human hepatocytes immortalized by SV40 T-Ag (Pfeifer et al., 1993) (FIG. 2). If the hepatocytes are sown at a low cell density as an individual cell suspension they show a stretched-out morphology. After cell-cell contacts formed the cells will reach a polygonal morphology similar to hepatocytes. After reaching confluence the cells will not form "three-dimensional foci" but scale off the pan surface. This points to the fact that a transformation of the cells has not taken place.

The established hepatocytes were designated as HepZ.

CHARACTERISTIC FEATURES OF THE ESTABLISHED HEPZ LINE

By means of immunofluorescence the established cells were analysed to state their hepatocyte-specific parameters. Primary human hepatocytes (fixed 24 hours after isolation—HuPrimHep) and the cells of the human HepG2 and HuH7 hepatoma lines were used for controlling. The results are presented in Table 1.

TABLE 1

Hepatocyte-specific markers of established human hepatocytes (HepZ) during immunofluorescence

| cells | CKN8 | CKN19 | Alb | AFP | AAT |
| --- | --- | --- | --- | --- | --- |
| HepZ | + | + | ++ | − | + |
| HuPriHep | + | + | ++ | − | ++ |
| HuH7 | + | + | ++ | ++ | − |
| HepG2 | + | + | ++ | ++ | − |

Primary human hepatocytes, HepG2 and HuH7 cells, were used for controlling.

Figure 3A:
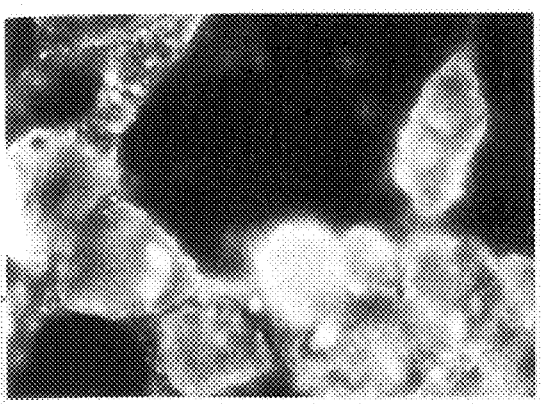
FIG. 3 Immunofluorescense analysis of the hepatocyte-specific marker in the established line of human hepatocytes HepZ. Primary human hepatocytes and cells of the human hepatoma lines HuH7 and HepG2 served for controlling. Albumin expression in a) HepZ, b) HuH7, c) HepG2, d) primary hepatocites, e) AFP expression in HepG2, f) absence of AFP expression in HepZ (enlargement 1:200)
Figure 3B:
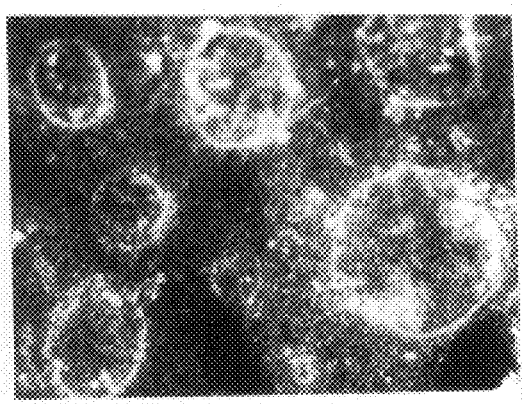
Figure 3C:
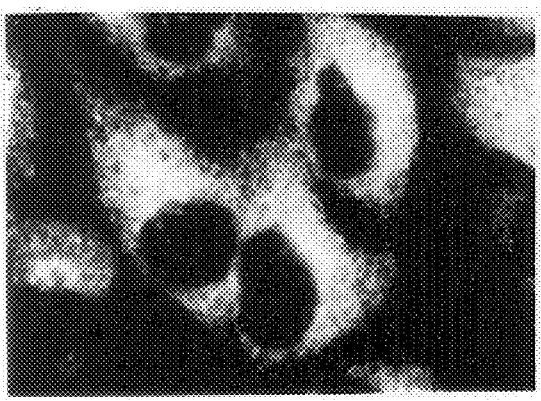
Figure 3D:
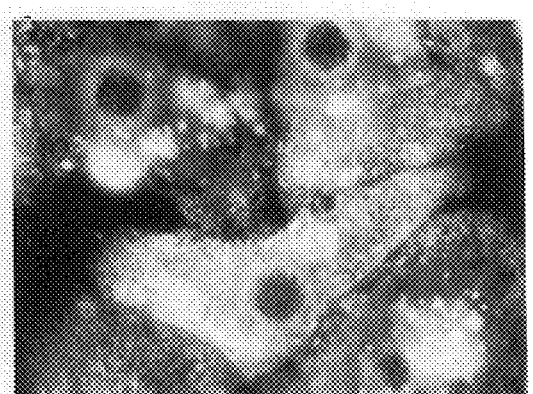
Figure 3E:
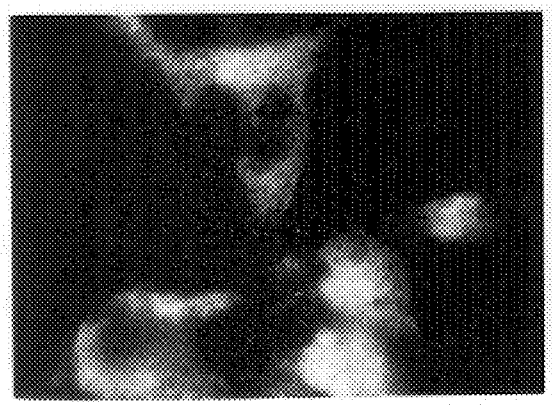
Figure 3F:
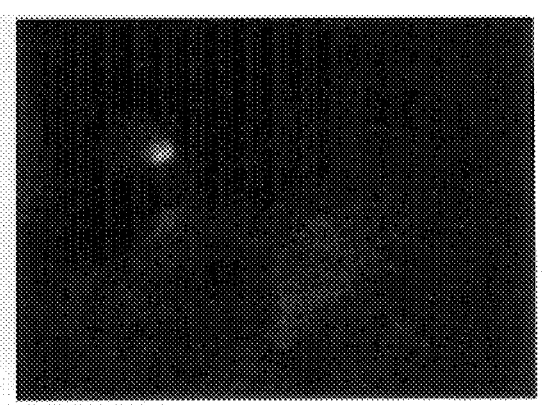

The table shows that HepZ (FIG. 3a) and HuH7 (FIG. 3b), HepG2 cells (FIG. 3c) and primary hepatocytes (FIG. 3d) are strongly positive for albumin. After 3 passages HepZ were still positive for alpha-1 -antitrypsin (AAT). Unlike cells of the hepatoma line HepG2 (FIG. 3e) HepZ are negative for fetoprotein (AFP) (FIG. 3f). This points to the fact that the established cells come from differentiated hepatocytes. All cells (also primary human hepatocytes) were positive for CKN8 and for CKN19. The HepZ line was also tested for the expression of p53 and pRb. The above-mentioned hepatoma lines (Tab. 2) served for controlling.

TABLE 2

Detection of the expression of the proteins pRb and p53 in HepZ cells by immunofluorescence

| cells | p53 | pRb |
| --- | --- | --- |
| HepZ | + | − |
| HuH7 | +++ | + |
| HepG2 | ++ | +++ |

HepG2 and HuH7 cells served for controlling.

Figure 4A:
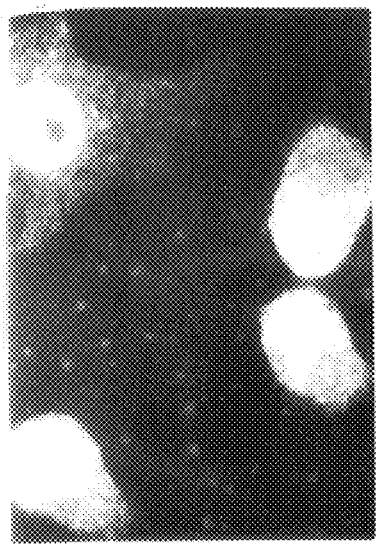
FIG. 4 Immunofluorescence analysis of the expression of p53 and pRb in HepZ cells The hepatoma lines HuH7 and HepG2 served for controlling. a) strong expression of the mutant p53 in HuH7 cells, b) expression of the wild type of p53 in HepG2, c) expression of p53 in HepZ cells. Expression of pRb in d) HepG2, e) HepZ (enlargement 1:200)
Figure 4B:
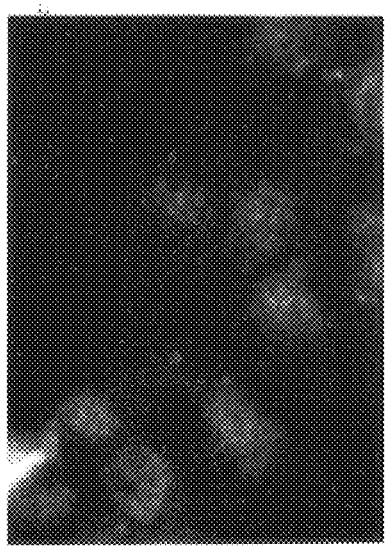
Figure 4C:
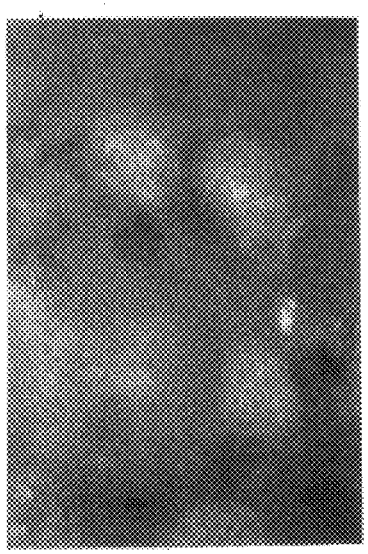
Figure 4D:
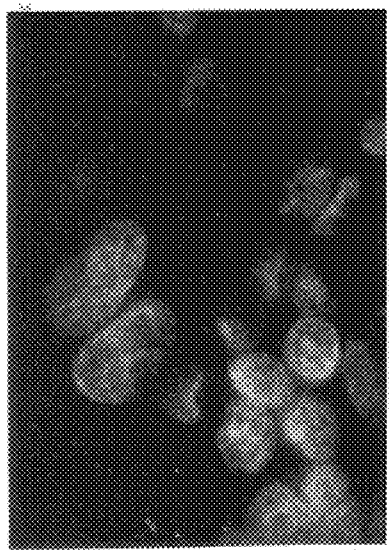
Figure 4E:
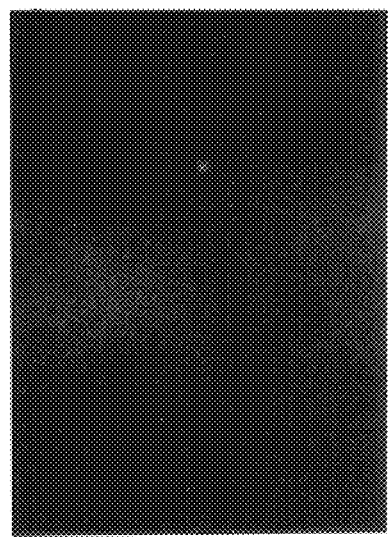
Figure 5:
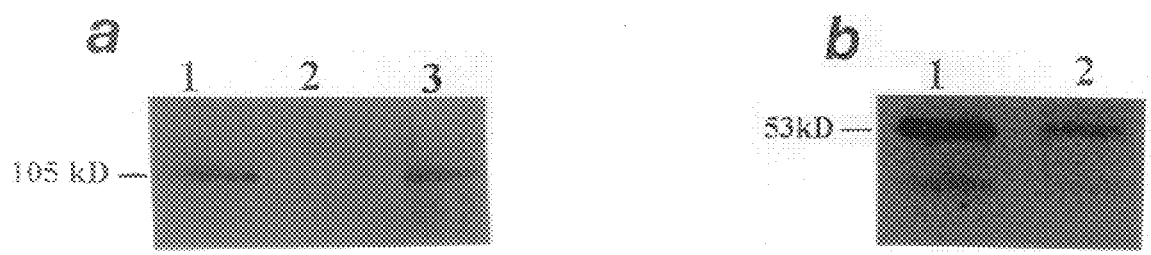
FIG. 5 Western Blot for the detection of pRb and p53 in established hepatocytes HepZ a) pRB expression, lane 1: HepG2 cells, lane 2: HepZ cells, lane 3: HuH7 cells, b) p53 expression, lane 1: HuH7 cells, lane 2: HepZ cells

A strong expression of the mutant p53 was detected in HuH7 cells (FIG. 4a) and an expression of normal p53 in HepG2 cells (FIG. 4b). HepZ cells were weakly positive for p53 (FIG. 4c). The HuH7 cells were weak and the HepG2 cells were strong for pRb (FIG. 4d). HepZ cells were negative for pRb (FIG. 4e). The elimination of pRb expression (FIG. 5a) and a reduction, however not a complete inactivation of the p53 synthesis (FIG. 5b) in HepZ cells, was also confirmed by means of Western Blot.

A weak expression of p53 does not result from the incomplete elimination of the expression by means of antisense constructions.

We claim:

1. A liver cell line HepZ (deposit no.: DSM ACC2302).

2. A method of making a liver cell line from primary human hepatocytes, comprising the steps:
   a) treating said primary human hepatocytes with hepatocyte growth factor to thereby effect a round of cell division, and
   b) subsequent or simultaneous transfection of the hepatocytes treated in step (a) with antisense coding recombinants AlbasRb and Albasp53.

3. The method according to claim 2, further comprising additional transfection of recombinants to thereby effect expression of one or both of cyclin D1 and E2F.

* * * * *